United States Patent [19]

Monett

[11] Patent Number: 4,640,272

[45] Date of Patent: Feb. 3, 1987

[54] SPRINGLESS DIAPHRAGMS AND METHOD OF PRODUCING SAME

[76] Inventor: Edward Monett, 639 Scotch Plains Ave., Westfield, N.J. 07090

[21] Appl. No.: 540,402

[22] Filed: Oct. 11, 1983

[51] Int. Cl.$^4$ ................................................ A61F 5/46
[52] U.S. Cl. ..................................................... 128/127
[58] Field of Search ......................................... 128/127

[56] References Cited

U.S. PATENT DOCUMENTS

| | | | |
|---|---|---|---|
| 2,256,602 | 9/1941 | Edwards | 128/127 |
| 2,294,589 | 9/1942 | Waterbury | 128/127 |
| 2,522,822 | 9/1950 | Harris | 128/127 |
| 2,529,363 | 11/1950 | Ballard et al. | 128/127 |
| 2,540,932 | 2/1951 | Clark | 128/127 |
| 2,580,133 | 12/1951 | Sheen | 128/127 |
| 2,697,057 | 12/1954 | Senger et al. | 128/127 |
| 3,042,029 | 7/1962 | Johansson | 128/127 |
| 3,169,522 | 2/1965 | Monett | 128/127 |
| 3,169,894 | 2/1965 | Monett | 128/127 |
| 4,007,249 | 2/1977 | Erb | 128/127 |
| 4,261,352 | 4/1981 | Sedlacek | 128/127 |
| 4,300,544 | 11/1981 | Rudel | 128/127 |
| 4,326,510 | 4/1982 | Buckles | 128/127 |
| 4,450,836 | 5/1984 | Goepp et al. | 128/127 |

*Primary Examiner*—Gene Mancene
*Assistant Examiner*—C. W. Shedd
*Attorney, Agent, or Firm*—Jack B. Murray, Jr.

[57] ABSTRACT

The present invention provides a springless diaphragm which is adapted to be inserted into a vaginal vault for birth control and which comprises a resilient rim member composed of a first flexible material, and a dome member which is composed of a second flexible material. The rim member is securely bonded to the dome member and extends continuously thereabout along the lower perimeter thereof. The dome member is provided in its uppermost portion with a substantially thicker portion in order to permit formation of the device without danger of rupture during the molding process. The first flexible material and the second flexible material are required to have Durometers within specified ranges, and the rim member may be further provided with opposing outwardly projecting sections in order to enhance the spring modulus of the rim member upon flexing of this portion of the diaphragm prior to insertion.

14 Claims, 11 Drawing Figures

SPRINGLESS DIAPHRAGMS AND METHOD OF PRODUCING SAME

BACKGROUND OF THE INVENTION

1. Field of the Invention

This invention relates generally to diaphragms having springless rims, and more particularly to springless rimmed diaphragms which provide dome shaped portions affixed to the rims and especially adapted for use in birth control.

2. Description of the Prior Art

Conventionally used diaphragms are provided with a dome shaped body portion and a rim which is reinforced with a coiled spring imbeded therein. Diaphragms have been in wide-spread use as birth control devices for over fifty years, and during this time the industry has not made any appreciable change in the form, shape or method of manufacturing of these diaphragms. The commercial diaphragms are all round in shape and contain such coiled springs in the rims thereof, and are typically made of natural rubber.

In the conventional manufacturing method, a spring coil of the desired size is encapsulated in gum rubber, but the resulting combination is not vulcanized until the dome is formed and joined to the rim. This is accomplished by placing the encapsulated rim into a suitably sized mold which is provided with a dome shaped portion. An additional quantity of the gum rubber is then added to the mold which is then closed under heat and pressure to force this additional quantity of rubber downwardly over the dome portion of the mold and to bond the thus-molded dome to the spring-rim combination, by vulcanization.

In the construction of the above type of diaphragms, extreme problems have existed over the years in successfully producing spring rimmed devices with any reasonable degree of reliability and efficiency, and there has resulted a need to discard a high percentage of the products so produced due to flaws in the molded products, particularly in the spring rimmed portions thereof. As a result of this procedure and the attendant extremely high rate of discards, devices of the conventional type have been merchandised at a high price.

From experiences with molding devices in which such spring rimmed portions are provided, it has been substantially impossible to locate the spring, constituting an integral part of the rim, centrally within the finally vulcanized rim. In many instances, part of the spring would be exposed at the periphery of the rim, or would be so close to exposure as to render the molded product a reject upon inspection thereof. The failure to locate the spring centrally in the molded rim necessitates rejection of the molded product since corrosion of the spring is a possible consequence of incomplete encapsulation with the gum rubber after vulcanization. Also, the wearer of the device can experience some discomfort due to irritation which can result to sensitive body surfaces which come into contact with any exposed spring sections. Of course, the exposed springs could also serve as the focal point for collection of bacteria which would make sterilization of the devices more difficult, and even if such disadvantages could be successfully overcome, the exposed springs would not be aesthetically acceptable to the user.

Illustrative of the various diaphragms which have been heretofore proposed are those disclosed in U.S. Pat. No. 2,087,610 which relates to devices composed of flexible resilient material such as rubber and provided with an oval shaped rim comprising a coiled spring imbeded in a bead-like rim composed of the diaphragm material. The rim is provided with an off-center pocket or dome adapted to be filled with an antiseptic jelly before the diaphragm is inserted into the wearer.

U.S. Pat. No. 2,529,363 relates to a diaphragm having a complex arrangement of an expansible helical spring and wires in the rim of the device which is in turn composed of soft rubber or latex.

U.S. Pat. No. 2,540,932 illustrates the complexity in the manufacturing methods employed by the prior art. An oval helical spring is assembled with two opposing flat springs positioned therewithin. Since machining of oval shaped molds is expensive, the patentee employs a circular shaped mold and forces the oval spring assembly onto the circular mold. The molding operation by closing the mold and forming the dome portion and vulcanizing the device, followed by removal of the device from the mold, whereupon the rim then is allowed to resume its oval shape. Such distortion of the oval spring during the molding operation can result in an increased tendency of the spring to come to the surface of the rim bead, thereby leading to rejected molded products.

In U.S. Pat. No. 2,294,589, the patentee employs an oval shaped die onto which the spring assembly is placed prior to encapsulation of the spring and formation of the dome portion of the diaphragm. Again, this method does not avoid the problems associated with the high turbulence during application of heat and pressure in the molding step which causes the above-noted exposure of springs in the finally molded diaphragm.

The devices of U.S. Pat. No. 3,169,894 emloys two opposing pins within the coiled spring, and U.S. Pat. No. 3,169,522 molds an additional portion of the diaphragm material on the dome at the lower periphery thereof to allow the molded product to be withdrawn from the mold and the rim-spring portion to be rolled up one complete turn to ensure that the spring is fully covered by the rubber. The resulting device in U.S. Pat. No. 3,169,522 is then treated to bond the turned up rim onto the dome.

The more recent attempts at improvements in the conventional devices have not curred the above discussed difficulties of high rejection rates and also variously introduce additional complex steps in the manufacturing process.

In U.S. Pat. No. 4,261,352, the rim of the diaphragm houses an inner reinforcing ring, held loosely therewithin, one end of which is sized so as to telescope into the opposite end, to permit size adjustment.

U.S. Pat. No. 4,300,544 employs a rim which is discontinuous and which varies in thickness about the circumference thereof at the side in the rim which is opposite the anterior rim opening. In another embodiment, the rim is formed so as to provide overlapping ends. In these devices, the rim is bonded to a flat sheet member on which is provided a sponge which acts as the contraceptive when placed in the user.

SUMMARY OF THE INVENTION

According to the present invention, a springless diaphragm is provided which is adapted to be inserted into a vaginal vault for birth control and which comprises a resilient rim member composed of a first flexible material and a dome member composed of a second flexible material, said rim member being securely bonded to the dome member and extending continuously about the lower periphery of the dome member which projects upwardly therefrom. The dome member is provided in its uppermost central portion with a thicker portion in order to permit formation of the dome according to the method of this invention. The first flexible material is characterized by a high Durometer and the second material by a low Durometer, and the device therefore achieves improved results without the need to include a spring within the rim, as was required by the prior art. Therefore, the rim member is preferably solid. In a preferred embodiment, the rim is provided with two opposing, outwardly arched rim sections which have been found to impart further spring tension to the rim when the rim is flexed prior to insertion, and thereby further stabilizes the diaphragm within the vaginal vault.

DETAILED DESCRIPTION OF THE INVENTION

Figure 1:
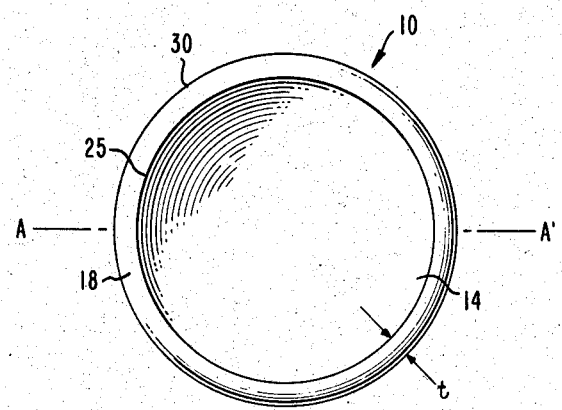
FIG. 1 is a plan view of one embodiment of the diaphragm of this invention which has a substantially circular shape.
Figure 2:
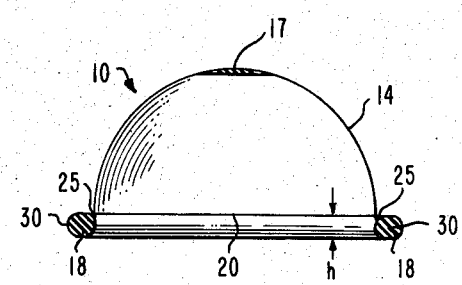
FIG. 2 is a cross-sectional, elevational view of the device of FIG. 1 taken along line A—A'.

Referring to FIGS. 1 and 2, there is illustrated one embodiment of the device of this invention, indicated generally at 10, which comprises dome 14 and rim 18. Dome 14 is formed so as to have a substantially circular lower periphery 25 and to be securely bonded to the inner portion of rim 18 which extends continuously and uniformly about the circumference of dome 14. Rim 18 is therefore also formed so as to provide a substantially circular outer edge 30. Dome 14 possesses a generally round shape, which is preferably uniform in curvature along its inner and outer surfaces. The uppermost portion of dome 14, indicated at 17, is preferably formed to be at least slightly thicker than the balance of dome 14 since this has been found to be generally necessary to minimize the possibility of rupturing the upper portion of the dome in separation of the molded dome from the mold as will be explained in more detail below.

Rim 18 and dome 14 are bonded so as to form a substantially smooth inner surface 20 about the inner periphery thereof. Such smooth inner surfaces geatly fascilitate the cleaning of the device and minimize the retention of foreign matter thereon during the subsequent manufacturing and packaging of the device or during its handling or use by the consumer.

Figure 7:
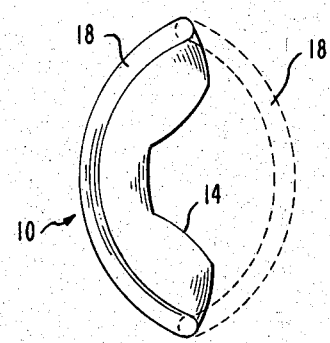
FIG. 7 illustrates the device of FIG. 1 in a folded position suitable for insertion, and is viewed elevationally.
Figure 8:
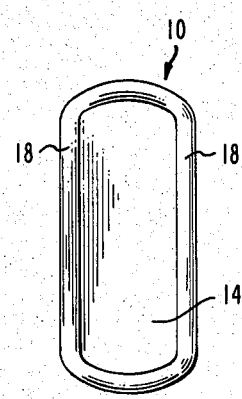
FIG. 8 is a plan view of the folded device of FIG. 7.
Figure 10:
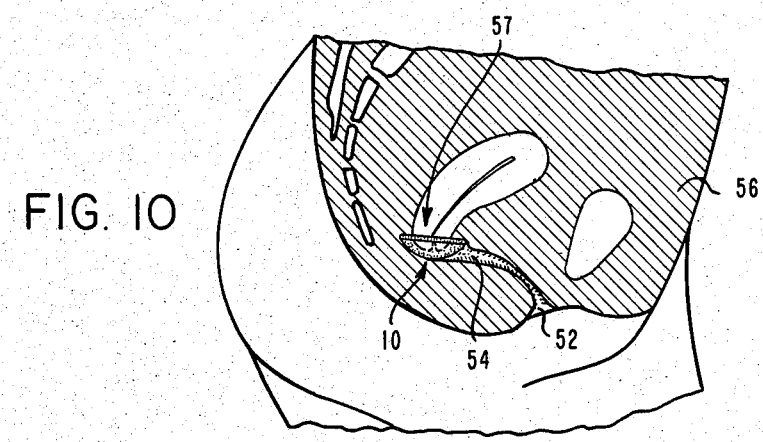
FIG. 10 is a sectional view of a female anatomy showing the vaginal vault with the device of FIG. 1 inserted therein.

In use, rim 18 of device 10 can be gripped by placing one's fingers on opposite sides thereof, causing the rim 18 to fold together when the gripped portions are squeezed. This results in a smaller cross-section, is illustrated in FIGS. 7 and 8, and eases the insertion of the folded device through the vagina 52 and into the vaginal vault 54 of the female 56, as illustrated in FIG. 10. Upon insertion, the pressure on rim 18 can be released and the rim 18 will then quickly spring back into its original form. The inserted diaphragm 10 can be positioned in the conventional manner in vaginal vault 54 to prevent sperm from passing upwardly from vaginal vault 54 into the opening of cervix 57, thereby acting as a barrier contraceptive.

After it has been used, the device 10 can be removed from vaginal vault 54 of the female in a manner similar to conventional devices, as for example by hand or by the use of any of the conventional removal instruments which are known in the art. The device 10 is then capable of being cleaned for reuse, as by washing in soap water and then boiling it in water or heating it in a sterilization autoclave. Preferably, device 10 is constructed of materials which will permit the repeated sterilization thereof without any substantial degradation of the materials' properties which would adversely affect either the performance of the device or the textual "feel" or visual appearance of the devices' surface (e.g., substantial darkening thereof) which could render the device aesthetically unacceptable to the user.

Rim 18 and dome 14 can be of any suitable size, which can vary widely depending on the size requirements of the vaginal vault 54 into which the device 10 is to be inserted for birth control. Generally, rim 18 will be of a diameter of from about 50 to 110 mm, and preferably of from about 60 to 90 mm, as determined by outside edge 30. Similarly, the dome 14 will be generally characterized by a curvature which corresponds to an effective diameter of from about 50 to 110 mm, and preferably of from about 60 to 90 mm. The thickness of rim 18 and dome 14 can also vary widely depending on such factors as the type of material selected for use in the construction of the devices 10 and other factors, and will generally range from about 5 to 8 mm for rim 18 (e.g., "t" in FIG. 1) and from about 0.3 to 0.5 mm for dome 14. Similarly, the height of rim 18 (e.g., "h" in FIG. 2) will generally range from about 5 to 8 mm. As shown in FIGS. 1 and 2, rim 18 can be characterized by an elongated cross-sectional shape in which rim thickness dimension "t" is greater than rim height dimension "h". Also, as will be seen in FIG. 4, in connection with rim 118, the rims can be characterized by a circular cross-sectional shapes in other embodiments of the springless diaphragms of this invention. The upper, thicker portion 17 of dome 14 will generally be from about 40 to 300%, and preferably from about 150 to 250%, thicker than the balance of dome 14 to prevent the dome from being ruptured during removal of the excess molding resin from the transfer molding device after molding of the device 10, as will be explained in more detail below. Also, the upper, thicker portion 17 of dome 14 will be of a similar circular shape to dome 14 (as viewed in plan view as in FIG. 1) and will be centered about the vertical longitudinal axis of dome 14. Portion 17 will generally occupy from about 1 to 10 percent of the total area of dome 14 as projected in plan view, as in FIG. 1.

It will be understood that dimensions outside the foregoing ranges can also be used if desired.

Device 10 can be made of any convenient material such as plastic, which may be for example, polyethylene, polypropylene, polybutylene, polyvinylchloride or like materials which possess the desired properties, as will be explained in more detail below. Especially preferred as the material for construction of the devices of this invention is silicone rubber, and most especially a pharmaceutical grade silicone rubber.

The color of the device 10 is important in terms of establishing consumer acceptance of the molded product. Thus, a rubber material which is black or dark colored in its molded form is generally not acceptable to the end user. Suitable materials of construction, therefore, provide molded devices 10 which have a light color, such as white, off-white, light tan, pale blue, pale pink, pale yellow and the like, with white being especially preferred.

Rim 18 should be constructed of material which is substantially chemically inert to body fluids, and has a high tear strength, low compression set, low permanent set and high Durometer. Preferably, rim 18 is constructed of silicone rubber having the following properties:

TABLE 1

| Property | Rim Properties | |
|---|---|---|
| | Range | Test Method |
| Ultimate tensile strength, psi | 1070–1200 | ASTM D412, Die C |
| Ultimate elongation, % | 92–110 | ASTM D412, Die C |
| Compression set, % | 10–12 | ASTM D395, Method B, 22 hours at 158° F. |
| Hardness, Shore A Durometer | 75–90, preferably 85–90 | ASTM D2240-64T |
| Tear strength, ppi (pounds per inch) | 95–105 | ASTM D624-Die C |

Similarly, dome 14 should be constructed of a material which is substantially chemically inert to body fluids, has a high tear strength and a very low permanent set. The material of dome 14 should be very soft and skin-like to the touch and should have a low Durometer. Preferably, dome 14 is constructed of silicone rubber having the following properties:

TABLE 2

| Property | Dome Properties | |
|---|---|---|
| | Range | Test Method |
| Ultimate tensile strength, psi | 1250–1350 | ASTM D412-Die C |
| Ultimate elongation, % | 600–750 | ASTM D412-Die C |
| Compression set, % | 3–5 | ASTM D395-Method B, 22 hours at 158° F. |
| 300% Modulus of elasticity, psi | 600–700 | ASTM D412-Die C |
| Hardness, Shore A Durometer | 35–50, preferably 35–40 | ASTM D2240-64T |

TABLE 2-continued

| Property | Dome Properties | |
|---|---|---|
| | Range | Test Method |
| Tear Strength, ppi | 190–210 | ASTM D624-Die C |

The foregoing combination of properties in the rim and dome portions of the devices of this invention has been found to result in a springless diaphragm which gives improved performance and which can be manufactured without the low efficiency and the high costs which have plagued the prior art devices. It will therefore be seen that the rim 18 and dome 14 of this invention are constructed of different materials which have distinctly different properties, unlike the prior art which formed spring containing devices using materials of construction to mold these devices which were the same throughout the molded article.

Exemplary of the especially preferred silicone rubbers useful in construction of the devices of this invention are dimethyl and methyl vinyl siloxane copolymers and blends of dimethyl polysiloxane and methyl vinyl polysiloxane reinforced with fumed silica fillers and containing peroxide catalyst (e.g., dicumyl peroxide) to accomplish the vulcanization. Such silicone rubber elastomers can be formulated employing conventional techniques to obtain the desired properties, such as those set forth in Tables 1 and 2, for silicone rubbers intended for use in rim 18 and dome 14, respectively.

Preferably, rim 18 and dome 14 are formed such that a pressure of from about 20 to 35 ounces of force on opposing sides of rim 18 are required to force such opposing rim sides together to form a folded shape such as in FIGS. 7 and 8.

Figure 11:
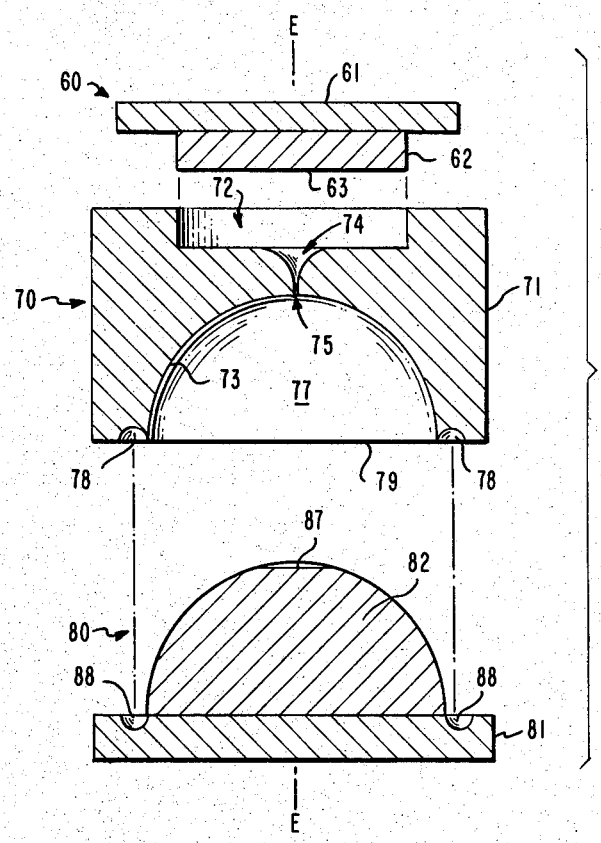
FIG. 11 is a cross-sectional elevational view, in exploded form, of a single cavity transfer molding apparatus for use in forming the diaphragms of this invention.

Referring to FIG. 11, there is illustrated a transfer molding apparatus, indicated generally at 90, for molding the diaphragm 10 of FIGS. 1 and 2. Molding apparatus 90 comprises circular base section 80, female mold section 70 and closure member 60. Base section 80 is provided with circular base 81, male dome mold member 82 having the desired (e.g., semispherical) shape and selected size, which projects upwardly from base 81, and circumferentially positioned rim channel 88, which is provide in base 81 about the lower periphery of male dome member 82. A circular depression 87 is provided in the uppermost portion of dome mold 82 to permit the molded dome 14 to have a thicker portion 17 at such an uppermost position, as has been described above. The center of circular depression 87 coincides with the vertical longitudinal axis 'E' of dome mold 82. Female mold section 70 comprises cylindrical housing 71 having the desired (e.g., semispherical) shaped dome cavity 77 extending upwardly therein from the lower periphery 79 of housing 71 and defined by inner surface 73. Mold section 70 is also provided with a circular resin chamber 72 and sprue cavity 74, which communicates resin chamber 72 with dome cavity 77 by means of sprue hole 75, which is preferably positioned along the vertical longitudinal axis 'E' of apparatus 90. An upper circular rim channel 78 is provided in the lower surface 79 of housing 71 about the lower periphery of dome cavity 77. Closure member 60 comprises circular plug 62 and circular plate 61. Plug 62 is adapted for insertion into circular resin chamber 72 during the molding operation, as will be explained in more detail below. The dimensions and shape of male dome member 82, dome cavity 77 and rim channels 88 and 78 will be selected in order to form the desired device 10 dimensions. Thus, the curvature and diameter of cavity 77 will be sufficiently larger than those of male dome mold member 82 to provide a molded dome 14 having the desired shape and thickness. Similarly, the dimensions and shape of lower rim channel 88 and upper rim channel 78 will be such as to provide a molded rim 18 of the desired shape and dimensions, and the size, location and shape of depression 87 will be similarly dictated by these parameters of the upper thicker portion 17 of dome 14 which is to be molded.

In operation of mold 90, a bead of non-cured or unvulcanized high Durometer silicone rubber (see Table 1) having the desired length is placed into lower rim channel 88. Housing 71 is then lowered onto base 81 so that the thus-positioned rim bead will be also positioned within upper rim channel 78. The length of the bead so positioned should be sufficient to provide a uniform continuous rim 18 when the molding operation is completed. A selected quantity of low Durometer silicone rubber (see Table 2) is then placed into circular chamber 72, after which closure member 60 is positioned upon cylindrical housing 71, and heat and pressure are then applied to the closed mold in a manner and for a time sufficient to force the silicone rubber downwardly out of chamber 72 through sprue cavity 74 and sprue hole 75 into the narrow cavity remaining between surfaces 73 of housing 71 and dome mold member 82, thereby forming the dome 14 and simultaneously bonding the thus-formed dome 14 to rim 18 along the lower periphery 25, to form a smooth inner surface 20 at the inner periphery of dome 14. The application of the heat and pressure also causes the bead to vulcanize, thereby forming the rim. The precise times, temperatures and pressures necessary to form the molded device 10 will be apparent to one of ordinary skill in the art and can be readily determined for a given material or resin by routine experimentation. Generally, times of from about 2 to 15 minutes and temperatures of from about 120° to 180° C. will be sufficient. Pressures of from about 30 to 250 tons will be sufficient, depending on the number of cavities in the mold, with lesser pressure in this range being needed for single cavity molds.

The thus-molded diaphragm 10 can be removed from mold 90 by lifting closure member 60 from housing 71, removing any excess rubber from cavities 74 and 72 and separating housing 71 from base section 80. The molded diaphragm can be removed from dome mold member 82 and lower rim channel 88 using conventional techniques, such as by use of compressed air streams directed so as to dislodge the lower portion of the rim and dome from the associated mold parts. The rubber contacting surfaces of the mold can be treated, if desired, with any of the conventionally used mold lubricants to fascilitate opening of the mold and removal of the molded device therefrom. Preferably the molded diaphragm is removed from the mold while the mold is still at substantially the temperature used in the molding step.

When removing the excess rubber from chamber 72 after completion of the molding operation, the excess in chamber 72 will be vulcanized to the remaining rubber in sprue cavity 74, and hence will be in contact with the upper portion of the dome in cavity 77 at the upper portion of the dome, at 17. Therefore, the upper thicker portion 17 is provided herein to prevent the removal of such rubber excesses from causing pull-through or rupture of the dome at the point therein at which the dome adjoins sprue hole 75.

Figure 3:
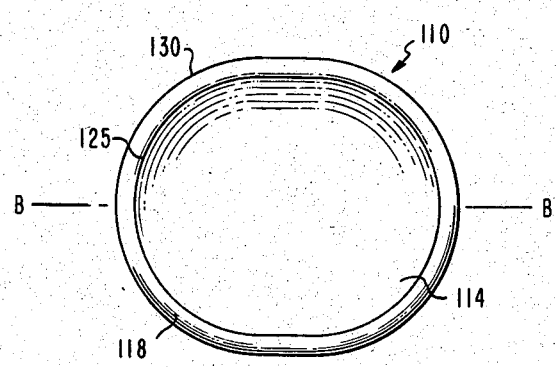
FIG. 3 is a plan view of a second embodiment of the diaphragm fo this invention which has a substantially oval shape.
Figure 4:
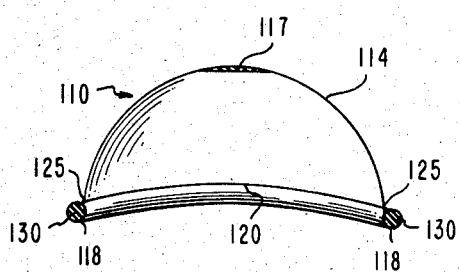
FIG. 4 is a cross-sectional elevational view of the device of FIG. 3 taken along line B—B'.

Turning now to FIGS. 3 and 4 there is illustrated a second embodiment of the device of this invention, indicated generally at 110, which comprises rim 118 and dome 114. In this embodiment, rim 118 is of a substantially oval shape, having a substantially oval shaped outer edge 130, and dome 114 and dome portion 117 are each oval shaped, as viewed in the plan view, as in FIG. 3. As in device 10, upper thicker portion 117 serves to prevent rupture of the dome material during manufacture. In other respects the construction, operation and use of device 110, and its method of manufacture, is the same as described above for device 10. Thus, rim 118 and dome 114 form a substantially smooth inner surface 120 about the lower periphery of dome 114, and the deformation of rim 118 by the application of force to opposing sides of rim 118 results in the folded shape as shown for device 10 in FIGS. 7 and 8. The oval shape of device 110 can be especially useful for conforming to the generally oval shaped dimensions of most vaginal vaults 54.

Generally, rim 118 will be from about 65 to 95 mm along its major axis, in its outside dimensions (as viewed in plan, as in FIG. 3), and from about 60 to 90 mm along its minor axis. Dome 114 will then preferably be of uniform curvature and have an effective diameter of from about 50 to 80 mm, and more preferably of from about 55 to 85 mm, along its major axis. Rim 118 may be substantially flat (not shown), as is rim 18 in device 10. Alternatively, rim 118 can be curved, either concave or convex, as illustrated in FIG. 4. When curved, the radius of the rim curvature is preferably from about 150 to 210 mm. The materials of construction and the method of manufacture and use of device 110 is the same as described above for device 10, except that the mold 90 will employ a suitably oval shaped mold member 82, cavity 77 and rim channels 78 and 88.

Figure 5:
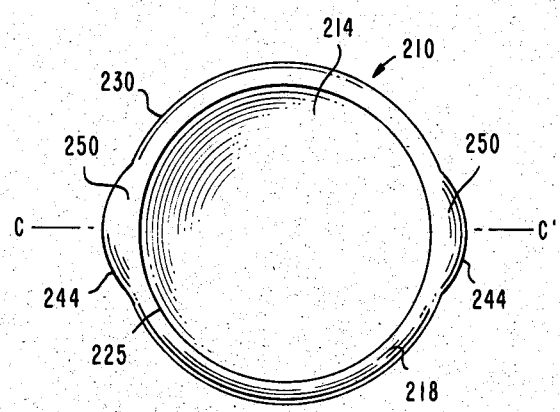
FIG. 5 is a plan view of a third and preferred embodiment of the diaphragm of this invention which is provided with a substantially round dome and a substantially circular rim which is provided with two opposing, outwardly projecting arched rim portions.
Figure 6:
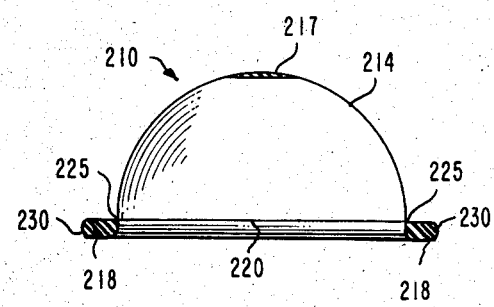
FIG. 6 is a cross-sectional elevational view of the device of FIG. 5 taken along line C—C'.

In FIGS. 5 and 6 there is illustrated yet another, and preferred, embodiment of this invention, indicated generally at 210, which comprises a rimmed portion 218 and a dome portion 214. Dome 214 is of a substantially round shape (semispherical) and has therefore a substantially circular lower outer periphery 225. Dome 214 is bonded securely along 225 to the rim 218, and as before is bonded therealong so as to form a substantially smooth inner surface 220 about the inner periphery of dome 214. Also, dome 214 is preferably formed so as to have a substantially thicker portion 217 at the uppermost part thereof, but is uniform in thickness otherwise.

Figure 9:
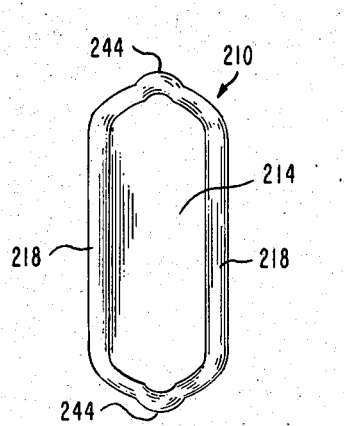
FIG. 9 is a plan view of the device 210 of FIGS. 5 and 6 in a folded position suitable for insertion.

Rim 218 in device 210 is uniformly round about its inner perimeter at 225 to accomodate the uniformly round dome 214. However, its otherwise circular outer perimeter 230 is provided with two opposing, outwardly projecting portions 244, each of which are preferably arched away from dome 214. Rim 218, which comprises arched rim sections 244 and circualr rim sections positioned therebetween, forms one continuous article about the lower periphery of dome 214. When so constructed, it has been found that the increased mass of rim material (e.g., rubber) at sections 244 increases the spring-modulus (i.e, the tension) of rim 218 in its deformed positioned, as indicated in FIG. 9, to enhance the ability of device 210 to remain securely positioned within the vaginal vault 54. Furthermore, outwardly projecting sections 244 provide the important function of engaging more accurately than a circular rim the pubic bone of the female when positioned within vaginal vault 54, thereby insuring that device 210 will remain in place to accomplish its intended birth control function. The enhanced spring tension imparted to rim 218 by sections 244 also enables a given spring tension to be obtained using a rim of smaller cross sectional area than can be produced by a continuously circular rim in the absence of such outwardly projecting sections 244. Hence, the rim 218 of a desired tension can be formed using a lesser amount of mass of the selected material from which the rim is to be molded.

The dimensions of dome 214 and rim 218, and the method of manufacture and use of device 210 is substantially the same as described above for devices 10 and 110. Also, the dimensions and shape of outwardly projecting rim sections 244 can vary widely. Thus, although arched sections 244 are illustrated and are preferred, it will be seen that rim sections 244 which are of a different shape (e.g., having planar rather than arched out edges) can be used. In device 210, sections 244 when arched will generally have a radius of curvature of from about 10 to 30 mm, and rim sections 244, regardless of shape, will generally each occupy from about 5 to 30 percent, and preferably from about 10 to 20 percent, of the circumference of rim 218, as determined along the outer periphery 230. The thickness of such sections 244 will generally comprise from about 105 to 200%, and preferably from about 115 to 170% (as measured along axis C—C' when viewed in plan, as in FIG. 5) of the thickness ("t") of the balance of rim 218. As in devices 10 and 110, rim 218 and dome 214 in device 210 are preferably formed in a size and shape and from materials such that a pressure of from abaout 20 to 35 ounces of force on opposing sides of rim 218 (in a direction which is normal to axis C—C' in FIG. 5) is required to force such opposing sides together to form a folded device 210, such as is illustrated in FIG. 9, for insertion.

The foregoing description has been given for the purposes of understanding only, and it will be understood that no unnecessary limitations should be read therefrom, as some modifications will be apparent from the above description. For example, and not by way of limitation, it will be understood that rim 218, which is shown in FIGS. 5 and 6 as being circular and flat, can be constructed in a curved manner, similar to the curvature provided in rim 118 in embodiment 110 in FIG. 4, or can be constructed in an oval manner, similar to the rim 118 shape in device 110. Likewise, dome 214 can also then be constructed in a related oval shape.

I claim:

1. A springless diaphragm adapted to be inserted into a vaginal vault for birth control which comprises (a) a resilient rim member composed of a first flexible rubber material, and (b) a dome member composed of a second flexible rubber material, said rim member being securely bonded to, and extending continuously about the base of said dome member, said dome member in the upper portion thereof having a greater thickness than the remainder of said dome member, said first rubber material being characterized by a Shore A Durometer of from about 75 to 90, and said second rubber material being characterized by a Shore A Durometer of from about 30 to 45.

2. The springless diaphragm according to claim 1 wherein said rim member is substantially circular and said dome member is substantially hemispherical.

3. The springless diaphragm according to claim 1 wherein said rim member and said dome member are each substantially oval in shape.

4. The springless diaphragm according to claim 1 wherein said thicker upper dome portion has a thickness of from about 40 to 300% greater than the thickness of the remainder of said dome.

5. The springless diaphragm according to claim 1 wherein said first material and said second material each comprise silicone rubber.

6. The springless diaphragm according to claim 1 wherein said rim member is provided with two opposing, outwardly projecting rim sections, each said projecting rim section extending outwardly from said dome member and being adapted to provide improved spring tension to said rim member when said rim member is flexed.

7. The springless diaphragm according to claim 6 wherein each said outwardly projecting rim sections is arched and comprises from about 5 to 30 percent of the total circumference of said rim member.

8. The springless diaphragm according to claim 7 wherein said arched rim sections are each characterized by a curvature radius of from about 10 to 30 mm, and wherein said rim member is circular and possesses a diameter of from about 50 to 110 mm.

9. The springless diaphragm according to claim 8 wherein said rim is solid and is further characterized by a thickness of from about 5 to 8 mm. and a height of from about 5 to 8 mm, as viewed in elevational cross-section.

10. The springless diaphragm according to claim 9 wherein said thicker upper dome portion occupies from about 1 to 10 percent of the total area of said dome member, as viewed in plan, and is centered about the vertical axis of said dome member.

11. The springless diaphragm according to claim 6 wherein said rim is constructed so that a compressive pressure of from about 20 to 35 ounces is required to force said rim together when said pressure is applied to the opposing sides of said rim in a direction normal to the axis connecting said opposing outwardly projecting rim sections.

12. The springless diaphragm according to claim 11 wherein said first material and said second material each comprise a pharmaceutical grade silicone rubber.

13. The springless diaphragm according to claim 1 wherein said rim member is characterized by a rim thickness and a rim height such that said rim thickness is greater than said rim height to provide said rim with a substantially elongated cross-sectional shape.

14. The springless diaphragm according to claim 1 wherein said rim member has a thickness of from about 5 to 8 mm, and a height of from about 5 to 8 mm, with the proviso that said rim thickness is greater than said rim height.

* * * * *